United States Patent [19]
Hart

[11] Patent Number: 5,876,917
[45] Date of Patent: Mar. 2, 1999

[54] DENDRITIC CELL-SPECIFIC ANTIBODIES AND METHOD FOR THEIR PREPARATION

[75] Inventor: Derek N. J. Hart, Christchurch, New Zealand

[73] Assignee: Canterbury Health Limited, Christchurch, New Zealand

[21] Appl. No.: 640,733

[22] PCT Filed: Nov. 4, 1994

[86] PCT No.: PCT/NZ94/00127

§ 371 Date: May 6, 1996

§ 102(e) Date: May 6, 1996

[87] PCT Pub. No.: WO95/12409

PCT Pub. Date: May 11, 1995

[30] Foreign Application Priority Data

Nov. 4, 1993 [NZ] New Zealand ............................ 250139

[51] Int. Cl.⁶ .......................... C07K 16/28; C07K 16/44; C07K 16/00; C12N 5/20

[52] U.S. Cl. .............................. 435/2; 435/975; 435/343; 435/343.1; 435/334; 436/512; 436/536; 530/388.22; 530/388.7; 530/388.73; 530/391.1; 530/391.3; 530/412; 935/104; 935/108

[58] Field of Search ................................ 435/2, 7.1, 7.21, 435/7.24, 975, 343, 343.1, 334, 104, 108; 436/512, 536; 530/350, 388.2, 388.22, 388.7, 388.73, 389.1, 389.6, 391.1, 391.3, 359, 412

[56] References Cited

FOREIGN PATENT DOCUMENTS

WO 93/04187  3/1993  WIPO .

OTHER PUBLICATIONS

B.Hock et al. Tissue Antigens, vol. 42 No. 4, Oct. 1993, p. 241.

J. McKenzie et al. Immunology, vol. 77 No. 3, Nov. 1992, pp. 345–353.

*Primary Examiner*—Ronald B. Schwadron
*Attorney, Agent, or Firm*—Nixon & Vanderhye

[57] ABSTRACT

This invention describes methods for generating antibodies specific for activation antigen CMRF-44 on activated dendritic cells, and antibodies produced by the method. The use of such antibodies, including monoclonal antibody CMRF-44, in immunological-based processes and systems for purifying and/or identifying activated dendritic cells is also described.

5 Claims, 5 Drawing Sheets

DENDRITIC CELL-SPECIFIC ANTIBODIES AND METHOD FOR THEIR PREPARATION

This application is a 371 of PCT NZ94/00127, filed Nov. 4, 1994.

FIELD OF THE INVENTION

This invention relates generally to immunological reagents (antibodies) capable of binding to dendritic cells, a method of generating such antibodies and to a process for identifying and purifying dendritic cells from blood using such antibodies.

BACKGROUND OF THE INVENTION

Dendritic cells constitute a distinct group of potent antigen presenting cells (APC) which are bone marrow derived and found as trace populations in the circulation as well as within both lymphoid and nonlymphoid tissues (1–3). Although their importance as the most effective haemopoietic cell involved in the initiation of primary immune responses has been well demonstrated (4–7), no human dendritic cell specific lineage marker has been identified and most features of their ontogeny and relationship to other leukocytes remains unclear.

Phenotypically, human dendritic cells are characterised (1–3,7–11) by a high density of class II MHC antigens, the presence of a wide range of adhesion molecules and the absence or low expression of a range of lineage specific cell surface antigens (CD3, CD14, CD16, CD19, CD57). A number of activation antigens including IRAC (12), HB15 (13), 4F2 (8), IL-2R (7,8), and B7/BB-1 (7,14) have also been reported on human dendritic cells, particularly after activation, although the anti-IRAC and HB15 reagents have not been shown to stain isolated fresh blood dendritic cells. Despite this phenotypic characterisation, identification and therefore purification of dendritic cells remains difficult as the majority of these antigens are expressed by other resting and activated cell types. Many of the functional and phenotypic features of dendritic cells are shared by both Hodgkins cells (HC) and Hodgkins Disease (HD) derived cell lines and there is increasing evidence to support the hypothesis, that in some instances, HC represent a malignant form of dendritic cell (15–17).

It is therefore an object of the present invention to inter alia provide a method of generating immunological reagents for use in a process for identifying and purifying dendritic cells.

Previous attempts to isolate antibodies specific for human dendritic cells have been largely unsuccessful. A number of these attempts have been directed toward monoclonal antibodies and have utilised an improved dendritic cell purification method to prepare immunogens (32) and a rapid two-colour flow cytometric screening procedure that allows large numbers of hybridoma supernatants to be examined in each fusion (33). These attempts failed, yielding only hybridomas that bind common antigens of both dendritic cells and other leukocytes.

Further attempts to generate dendritic cell-specific antibodies, in this case, through tolerisation of the host prior to immunisation with dendritic cells, have been reported (34). Two methods of tolerisation are compared. The first method involves the administration of a cytotoxic antiproliferative agent (cyclophosphamide(CP)) in conjunction with immunodominant leukocyte antigens to preferentially kill B cells that respond to unwanted epitopes. In the second method, tolerisation is induced by injecting the undesired immunodominant leukocyte antigens during the neonatal period.

It is reported that the first method generates only non-specific immunosuppression whereas the second method potentially leads to a state of antigen-specific non-responsiveness. However, the ability of the tolerised host to generate antibodies specific for dendritic cells is not demonstrated nor is any data provided regarding the efficiency of the method in producing a positive serological response to dendritic cells. All that is shown is tolerisation ie. lack of reactivity with T blasts.

The applicant's own investigations have however found that, in practice, an approach involving tolerisation of a neonate host with available immunodominant leukocyte antigens is not generally effective in raising immunologically useful antibodies against dendritic cells. In particular, the applicants attempts to tolerise neonatal mice with leukocyte antigen expressed on Epstein Barr Virus (EBV) transformed lymphoblastoid cell lines and to then raise specific antibodies against dendritic cells were unsuccessful.

This lack of success in generating dendritic cell-specific antibodies using the above approach is consistent with anecdotal reports of similar unsuccessful attempts made by other workers in this area.

Surprisingly, the applicants further investigations have found that when some monocytoid cell lines are used as the tolerising antigen in relation to a neonatal host, subsequent immunisation with dendritic cells or Hodgkins Disease derived cell lines does lead to the generation of antigen-specific antibodies. It is in part to this unexpected finding that the present invention is directed.

SUMMARY OF THE INVENTION

In a first aspect the present invention can be said to consist in a method of generating antibodies or fragments thereof which specifically bind to dendritic cells but not to peripheral blood leukocytes including the step of immunising an appropriate neonatal host animal tolerised to common cellular antigens through the administration of monocytoid cell line or a derivative thereof, with a Hodgkins Disease derived cell line or a dendritic cell foreign to said host animal.

Preferably, the monocytoid cell line is U937.

It is also preferred that the dendritic cells and peripheral blood leukocytes are human dendritic cells and human peripheral blood leukocytes.

It is particularly preferred that the neonatal host is immunised with Hodgkins Disease derived cell line L428.

Conveniently, the method includes the subsequent steps of:

(i) recovering splenocytes from said host animal; and
(ii) immortalising said splenocytes to form an immortalised cell-line secreting antibodies which specifically bind to dendritic cells but not to peripheral blood leukocytes.

Conveniently, step (ii) involves the fusion of said splenocytes with an appropriate myeloma cell line such as cell line NS-1.

In a further aspect, the present invention provides immortalised (hybridoma) cell lines obtained in accordance with the method defined above.

In still a further aspect, the invention provides antibodies which are produced in accordance with the method defined above.

In yet a further aspect, the invention provides hybridoma cell line CMRF-44.

In still a further aspect, the present invention provides monoclonal antibody CMRF-44 secreted by hybridoma cell line CMRF-44 which specifically binds to an epitope on activated human dendritic cells but does not bind to human peripheral blood leukocytes.

In yet a further aspect, the invention provides an antibody or antibody binding fragment which is specific for the epitope on human dendritic cells to which monoclonal antibody CMRF-44 binds.

In yet a further aspect, the invention provides an antibody or antibody binding fragment which is specific for an epitope on the activation antigen defined below.

In still a further aspect, the present invention provides a process for identifying and activated dendritic cells in a sample containing such cells comprising the step of contacting said sample with an antibody or antibody binding fragment as defined above.

In yet a further aspect, the invention provides a process for purifying and/or concentrating dendritic cells from a sample containing such cells comprising the step of contacting said sample with an antibody or antibody binding fragment as defined above.

In the preferred embodiment of these processes, the cells to be identified or purified are activated human dendritic cells and the antibody is monoclonal antibody CMRF-44.

In still a further aspect, the invention provides a dendritic cell purification system for use in purifying or concentrating dendritic cells from a sample containing such cells which includes an antibody or antibody binding fragment as defined above.

Conveniently, the purification system is designed to purify activated human dendritic cells and the antibody is optionally labelled monoclonal antibody CMRF-44.

In still a further aspect, the present invention consists in dendritic cells recovered by a process as defined above or by using a purification system as defined above.

In yet a further aspect, the invention provides an immunopotentiating composition comprising activated dendritic cells obtained as above and at least one antigen capable of generating a protective immunological response to a disease in an animal susceptible to such disease.

In still a further embodiment, the invention provides a method of prophylaxis and/or therapy in relation to a disease which comprises administering to a subject susceptible to said disease an immunopotentiating composition as defined above.

In yet a further aspect, the invention provides an assay kit which includes monoclonal antibody CMRF-44 for use as a diagnostic marker of activated dendritic cells.

In a final aspect, the present invention consists in an activation antigen:

(a) expressed by human dendritic cells containing an epitope to which monoclonal antibody CMRF-44 binds; or (b) expressed by dendritic cells of an animal other than a human which is biologically equivalent to antigen (a) and which is substantially homologous to antigen (a) in terms of its amino acid and/or nucleotide sequence.

BRIEF DESCRIPTION OF THE DRAWINGS

While the present invention is broadly as defined above, it will be appreciated that it is not limited thereto but that it also includes embodiments of which the following description provides examples. In addition, the present invention will be better understood by reference to the accompanying drawings which are as follows.

DESCRIPTION OF THE INVENTION

Figure 6:
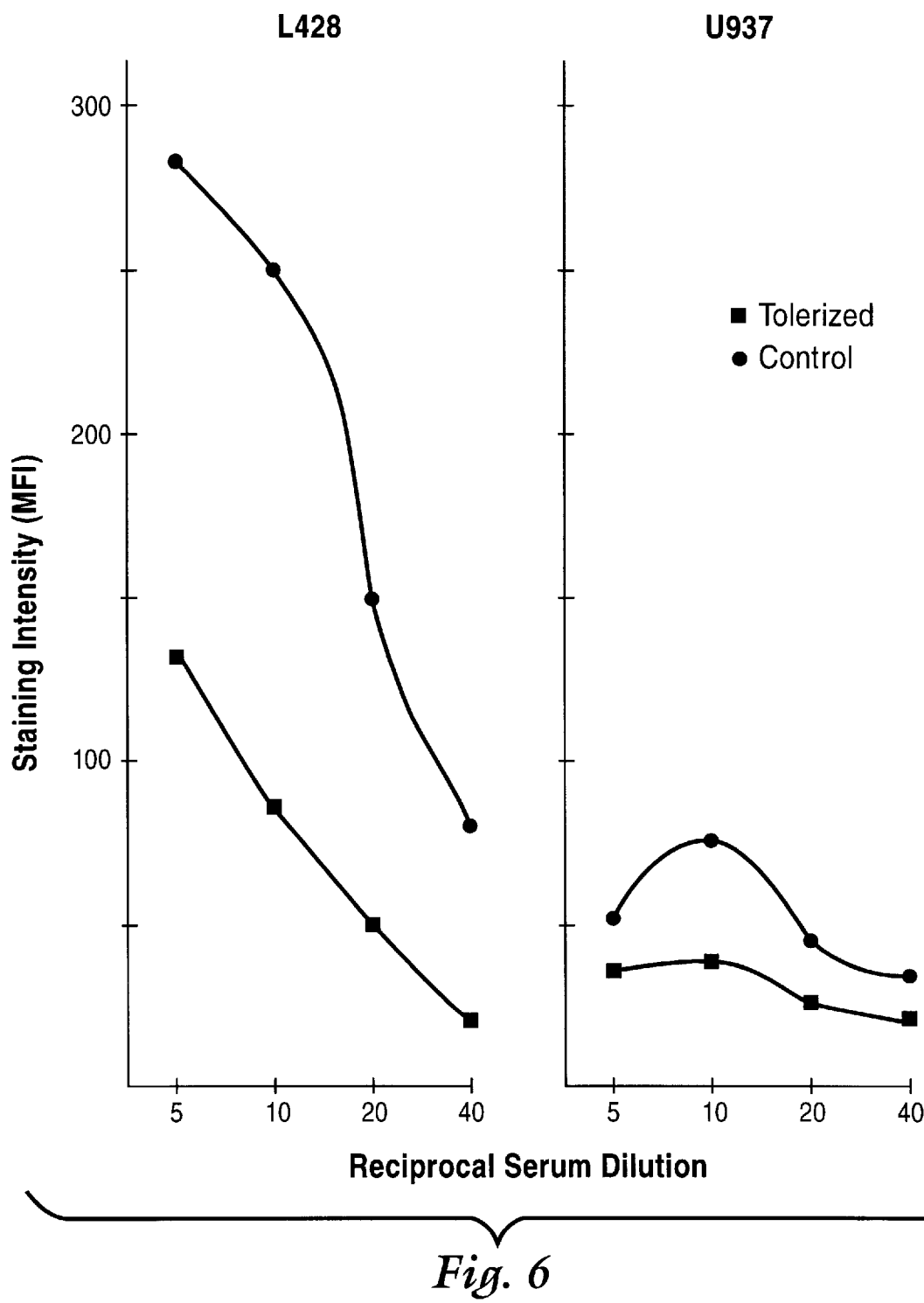
FIG. 6: Mice neonatally tolerized with the monocytoid cell line U937 have a specific serological response to the Hodgkins Disease derived cell line L428. The left panel indicates the mean fluorescence intensity (arbitrary units) of L428 cells labelled with either test mouse (○) ie U937 tolerized and L428 immunized serum or control (α) nontolerised but L428 immunised mouse serum and FITC sheep anti-mouse F(ab$^1$)$_2$ analyzed on a Coulter Epics flow cytometer. An amplified specific response to L428 occurs with the test serum (●) compared to the control serum (■) on the tolerizing cell line U937.

As indicated above, in a primary aspect the present invention provides methods of generating immunological reagents (antibodies) capable of specifically binding to dendritic cells (DC) but not to peripheral blood leukocytes. The critical aspect of the method is that the antibodies are generated by immunisation of a neonatal host animal (such as a mouse) following tolerisation of the host with a monocytoid cell line, preferably U937 or a derivative of this cell line. It has been the applicants surprising finding that tolerisation of the neonate with this cell line induces the host to mount an antigen-specific immune response upon subsequent immunisation of the host with a dendritic antigen (see FIG. 6).

By the term "neonatal" is meant an animal less than 72 hours old, more often less than 48 hours old, and preferably less than 24 hours old, in the case of a small animal, such as a rodent. It will be appreciated that in the case of a large animal host, such as sheep or goats, an animal may be considered to be neonatal if it is less than one month old, more often less than two weeks old, and preferably less than one week old.

Cell line U937 is a human monocytoid (monocyte-like) cell line derived from a histiocytic lymphoma (38) and is obtainable from the American Type Culture Collection, Rockville, Md. under accession No. CRL 1539. Other monocytoid lines are generally known in the art, and include, for example K562, HL60, KG1 and KG1a.

In the above method, the "dendritic cell antigen" with which the neonate is immunised can be either dendritic cells foreign to the host or a Hodgkin's Disease derived cell line. By "foreign to the host" is meant that the immunising dendritic cells are derived from a species other than the species to be immunized. For example, if it was desired to make antibodies to mouse dendritic cells, it would be preferable to immunize a species other than mouse, such as rat (for monoclonal antibody production) or rabbit for polyclonal antibody production. Preferably, the dendritic cell antigen will be a human antigen, more preferably human dendritic cells, most preferably Hodgkin's Disease derived cell line L428. This latter cell line is derived from a patient with nodular sclerosing Hodgkins Disease (39) and is obtainable from Professor Dr Volker Diehl, Karl-Wiechert-Allee 6, 3000, Hannover, Germany.

In a particularly preferred embodiment of the method, the tolerising cell-line U937 is preconditioned before being administered (usually by injection) to the neonatal host. This preconditioning involves activation by incubation in medium containing phorbol-ester, polymyristate acetate (PMA) and calcium ionophore A2318 (Sigma Chemicals).

It will be appreciated that the antibodies obtainable by the above method can be in the form of antisera containing polyclonal antibodies or, as is preferred, monoclonal antibodies may be obtained by use of hybridoma technology. Still further, antibodies or binding fragments can be produced using biochemical or recombinant DNA techniques.

Where it is desirable to obtain polyclonal antibodies, the immunisation protocol outlined above can be followed without augmentation, and antisera recovered using conventional techniques.

In the alternative, where it is desirable to obtain monoclonal antibodies or binding fragments of such antibodies, the general procedure of Kohler and Milstein (35) can be used. Generally, this procedure involves obtaining antibody-producing cells from the animal and fusing the antibody-producing cells with strains of myeloma cells to produce hybridomas. These hybridomas are grown or cultured to produce monoclonal antibodies specific for dendritic cells.

An example of the procedure using myeloma cell line NS-1 is given below. Cell line NS-1 is obtainable from Professor C Milstein, MRC Laboratory of Molecular Biology, Hills Road, Cambridge CB2 2QH, United Kingdom.

Other myeloma cell lines are known in the art and include, for example, the following cell lines: X63Ag8 653, SP2/0, FO and NSO/1. Cell lines which neither synthesise nor secrete immunoglobulin heavy or light chains (eg SP2/0) are generally preferred to cell lines which synthesise but do not secrete, immunoglobulin chains (eg NS-1).

If desired, antibody fragments can be prepared by controlled protease digestion of whole immunoglobulin molecules as described in Tjissen (36).

Alternatively, antibody fragments can be prepared using molecular biological techniques by isolating, from hybridoma cells, the genetic material encoding the variable regions of the heavy, light or both chains of the monoclonal antibodies and expressing them in suitable organisms for the product of recombinant antigen binding fragments (Fv, ScFv, Fab etc.) of the monoclonal antibody (Hodgson J, (37)).

By way of illustration of the method of the invention, the generation and characterisation of a monoclonal antibody, designated mAb CMRF-44, capable of binding to an epitope on an early activation antigen of human dendritic cells will now be described by way of example. From this description, those persons skilled in this art will also appreciate how other antibodies (or their binding fragments) can be obtained for use in the extraction of human DC or DC from other animals.

The term "substantially homologous" as used herein means at least 50% sequence homology, more often at least about 70% homology, and preferably about 80% or more sequence homology.

MATERIALS AND METHODS

Production of the CMRF-44 Monoclonal Antibody (CMRF-44 mAb)

Newborn Balb/c mice (<24 h) were tolerised to common cellular antigens by intraperitoneal (IP) injection with the monocytoid cell line U937. Five month old tolerised mice were immunised IP with the Hodgkins Disease derived cell line L428 and the splenocytes fused with the mouse myeloma line NS-1 five days later. The CMRF-44 mAb producing hybridoma was identified and cloned as described in the results. Isotyping was performed using the Amersham (Amersham, UK) isotyping kit.

Preparation of Cells

Peripheral blood mononuclear cells (PBMC) were prepared by density gradient centrifugation over FICOLL-HYPAQUE (F/H). Tonsil mononuclear cells were obtained from minced tonsils using FICOLL-HYPAQUE gradients. Blood and tonsil T lymphocytes were purified from mononuclear cells by SRBC rosetting and the non-SRBC rosetting fraction (ER$^-$) was used as a source of either enriched tonsil B cells or T cell depleted PBMC. Granulocytes were isolated from the pellet formed during F/H centrifugation of peripheral blood with contaminating RBC removed by hypotonic lysis.

Monoclonal Antibodies

The anti-CD3 (OKT3, IgG$_{2a}$), anti-CD25 (7G7/B6, IgG$_{2a}$), anti-CD19 (FMC63, IgG$_{2a}$), anti-CD57 (HNK-1, IgM) and anti-HLA-DR (L243, IgG$_{2a}$) antibodies were produced from hybridomas obtained from the American Type Culture Collection (ATCC, Rockville, Md.). The antibodies CMRF-7 (CD15, IgM), CMRF-15 (erythrocyte α sialoglycoprotein, IgM), CMRF-20 (anti-HLA class II, IgM), CMRF-11 (CD45RA, IgG$_1$), CMRF-31 (CD14, $IgG_{2a}$) and CMRF-2 (CD71, $IgG_1$) were produced and characterised by the applicants. Phycoerythrin conjugated Leu-16 (CD20) and leu 1 (CD5) antibodies were obtained from Becton Dickinson (Mountain View, Calif.) and phycoerythrin conjugated anti-CD14 and negative control ($IgG_1$, $IgG_{2a}$) antibodies were obtained from DAKO (Carpinteria, Calif.). The B1 (CD20) mAb was obtained from Coulter Immunology (Hialeah, Fla.) and BA1 (CD24) mAb was obtained from Hybritech Inc (La Jolla, Calif.). The anti-HB15a mAb ($IgG_{2a}$) (13) was a gift provided by Dr Thomas F Tedder (Dana-Farber Cancer Institute, Boston, Mass.). The BB-1 mAb (anti B7/BB-1,IgM) was a gift provided by Dr J A Ledbetter, Bristol-Myers Squibb PRI, Seattle, Wash. The anti-CD16 mAb, HUNK-2 ($IgG_{2a}$) was a gift from Professor I F C McKenzie, Melbourne, Australia.

Indirect Immunofluorescence

Cells ($<10^6$/test in PBS) were incubated with mAb for 30 minutes on ice, washed and incubated with fluoresceinated F(ab')2 sheep antimouse Ig at 30 $\mu$g/mL (FITC-SAM, Selenius Laboratories, Hawthorn, Australia) and washed prior to analysis on an EPICS 2 fluorescence activated cell analyser (Coulter Electronics, Hialeab, Fla.). Double labelling staining involved labelling with mAb and FITC-SAM followed by incubation (10 min) in mouse serum (10%), prior to adding a phycoerythrin conjugated mAb.

Tissue Staining by Immunofluorescence

Normal human tissue was obtained from post mortem specimens and snap frozen. Sections were cut (6 $\mu$m) and left to dry overnight then fixed in cold acetone for 10 minutes. Sections were incubated with mAb for 30 minutes, washed and then incubated further with FITC-SAM for 30 mins. Following washing and incubation in mouse serum (10 min), phycoerythrin conjugate or biotin conjugate was added for 30 mins.

Selection of Cell Populations by Cell Sorting

Cells were labelled with mAb as indicated in each experiment on ice for 30 min, then washed and incubated with FITC-SAM. Cells were then sorted at 4° C. on a FACS IV fluorescence activated cell sorter (Becton Dickinson, Mountain View, Calif.).

Isolation of Human DC

Tonsil DC were purified as described previously (8). Briefly ER⁻ tonsil cells were cultured overnight at 37° C. then separated on a BSA gradient and the low density cells harvested and labelled with B1 (CD20), BA1 (CD24), OKT3 (CD3) and CMRF-31 (CD14) antibodies. The negative cell population (DC) was then obtained by either FACS sorting or by immunomagnetic depletion of labelled cells with Dynabeads (M-450 Dynal, Oslo, Norway).

Blood DC were isolated from ER⁻ PBMC by either direct FACS cell sorting (14) or by conventional separation methods (11). Directly isolated DC populations were obtained by labelling of fresh ER⁻PBMC with a mixture of mAb to CD3, CD14, CD16, CD19 and CD57 and FACS sorting of the negative population. Conventionally isolated DC were prepared following O/N culture of ER⁻ PBMC at 37° C. The low density cells were obtained on a BSA (Intergen, N.Y.) gradient then depleted of Fc receptor positive cells and B cells by panning on plates coated with human and rabbit anti-human Ig respectively. The nonadherent cells were harvested and separated on a NYCOPREP™ 1.068 density gradient (Nycomed Pharma AS, Oslo, Norway). DC were further purified using an antibody mix in combination with FACS sorting as above.

Cell Lines

T cell lines (HSB-2, Molt 4 and Jurkat), EBV transformed B cell lines (WT49, Mann), Burkitt's lymphoma lines (Raji and Daudi) and myeloid lines (K562, HL60 and U937) were grown in medium (10% FCS in RPMI-1640 (Gibco, Auckland, New Zealand) supplemented with 2 mM glutamine, 0.06 g/l penicillin and 0.1 g/l streptomycin). The Hodgkins cell line L428 was obtained from Dr V Diehl (Clinik for Innere Medizine, Cologne, Germany) and the Hodgkins cell lines KM-H2 and HDLM-2 (grown in 20% medium) were obtained from Dr H G Drexler (German Collection of Micro-organisms and Cell Cultures, Braunschweig, Germany).

Enzyme and Inhibition Studies

The enzyme susceptibility of the CMRF-44 antigen was tested by incubating (37° C., 1 h) L428 and U937 cells in 2 mL PBS containing DNAse (Sigma, St Louis, Mo., 1 mg/mL) and either TPCK-treated papain (Sigma, 50 $\mu$g/mL), pronase (Calbiochem, San Diego, Calif.,50 $\mu$g/mL) or neuraminidase (Behring,Marburg, Germany, 0.1U/mL). Cells were washed (×3) in PBS and analysed by flow cytometry.

N-linked glycosylation of glycoproteins was blocked by incubating L428 (12 h, 37° C.) in medium containing either 0 or 10 $\mu$g/ml tunicamycin (Sigma) and the effect of this on antibody binding to L428 was assessed by flow cytometry.

Immunoprecipitation

Cells were surface labelled with sulfo-NHS-Biotin (Pierce, Rockford, Ill.) (18) or biosynthetically labelled with $^{35}$S (NEN, Boston, Mass.) (19) prior to solubilisation by incubation (1 h on ice) of cells ($4\times10^7$) in 1 ml lysis buffer (20 mM $Na_2PO_4$, 10 mM EDTA,2mM LAA (Sigma) 2 mM PMSF (Sigma), 0.02% $NaN_3$, pH 8.2) containing either 0.6% NP40, 1% TRITON X-100 or 0.25% CHAPS. Following centrifugation (100,000×g,1 h), solubilised proteins were immunoprecipitated by a modification of the method of Tedder et al (19) using rabbit anti-mouse Ig covalently coupled to CNBr activated sepharose 4B (RAM sepharose) (Pharmacia, Uppsala, Sweden). Following preclearing of the lysate by 3 h incubation with RAM sepharose, solubilised proteins were immunoprecipitated by overnight incubation with RAM-sepharose precoated with the appropriate mAb. Immunoprecipitates were washed either with lysis buffer alone (low stringency wash) or with higher stringency washes containing 0.5 NaCl or 0.05% SDS as described previously (19). Bound antigen was eluted with sample buffer and analysed by gradient SDS-PAGE in combination with either autoradiography or Western blotting. Biotin labelled proteins were visualised after transfer to a nitrocellulose membrane (18) by streptavidin-biotinylated horseradish peroxidase complex and the Enhanced Chemiluminescence Detection System (Amersham, Arlington Heights, Ill.) as described by the manufacturers.

Lipid Studies

Total lipid was extracted in chloroform: methanol: $H_2O$ as described by Magnani et al (20). The insoluble nonlipid fraction was resuspended in CHAPS lysis buffer and the lipid extract further separated by phase partitioning as described by Bligh and Dwyer (21). The upper, lower and interface layers were drawn off then dried under $N_2$ and resuspended in CHAPS lysis buffer. All extracts were clarified by centrifugation (10,000×g/10 min) then applied to nitrocellulose by slot blotting.

Slot Blotting

Whole cell lysates (prepared as described above) and lipid extracts were applied to nitrocellulose (Hybond C, Amersham) by slot blotting (Biorad, Richmond, Calif.) under vacuum. Nitrocellulose strips were blocked by incubation (1 h, 37° C.) with 10% goat serum (Gibco) in PBS (GS), then incubated with mAb diluted in GS. Strips were washed three times with PBS then incubated 1 h with peroxidase conjugated goat anti-mouse (Dako, Carpinteria, Calif.) diluted (1:1000) in GS. Following washing with PBS colour was developed with 3,3'-diaminobenzidine (Sigma).

Transfection Studies

COS-7 cells grown in media were plated on Nunc petri dishes to approximately 50% confluence. For 24 hours prior to transfection the cells were cultured in 10% Nuserum/RPMI 1640 (Collaborative Research Inc). Transfection was carried out by exposing the cells to 250 μM DEAE-dextran (Sigma), 400 μM chlorquine disphosphate (Sigma) and 500 ng DNA in 10% Nuserum/RPMI 1640 for 2 hours at 37° C., followed by 10% DMSO in PBS for 2 minutes at 37° C. Transfectants were cultured for 48 hours in media and cell surface expression was examined by indirect immunofluorescence.

In Vitro Stimulation

Lymphocytes were cultured in medium containing a number of different stimuli and then analysed by indirect immunofluorescence. Tonsil T lymphocytes were stimulated with PHA (Sigma) at 5 μg/mL. Tonsil and blood B lymphocyte preparations were stimulated with either the phorbol ester PMA (Sigma) at 25 ng/mL plus the calcium ionophore CaI A23187 (Sigma) at 500 ng/mL or anti human IgM immunobeads (10 μg/ml, Biorad, Richmond, Calif.). Activated monocytes were obtained by the culture of ER⁻PBMC in AB medium (2.5% AB serum/RPMI-1640) containing either 500 U/ml GM-CSF (Leucomax, a gift from Sandoz Pharma, Auckland, New Zealand), 1000 U/ml interferon-γ (a gift from Boehringer Ingelheim, Ingelheim, Germany), or or 10 μg LPS (Sigma). Monocyte activation was then analysed after double labelling with phycoerytirin conjugated CD14 mAb using flow cytometry.

Mixed Leucocyte Reaction

Graded doses of sorted mitomycin C treated cells were added to $1 \times 10^5$ allogeneic T lymphocyte responders in 96 well plates (Becton Dickinson, Lincoln Park, N.Y.) and an MLR performed as described previously (9). Labelled and unlabelled starting cells were included as controls.

RESULTS

Screening of Hybridoma Clones

Neonatally tolerised BALB/c mice were immunised with the Hodgkins Disease derived cell line L428. Following cell fusion clones producing mAb reactive with the cell line L428 were identified by indirect immunofluorescence. Producer clones were then screened on peripheral blood. Supernatant from one clone, designated CMRF-44, was found to react with Hodgkins Disease derived cell lines but not with peripheral blood leukocytes. The hybridoma clone CMRF-44 was cloned by limiting dilution and passaged into BALB/c mice to produce a malignant ascites. The mAb CMRF-44 was determined to be of the IgM isotype.

Hybridoma CMRF-44 has been deposited at the American Type Culture Collection, 12301 Parklawn Drive, Rockville, Md. 20852, United States of America on 1 Nov. 1993 under Accession No. ATCC CRL 11482.

CMRF-44 Reactivity on Isolated DC

Figure 1A:
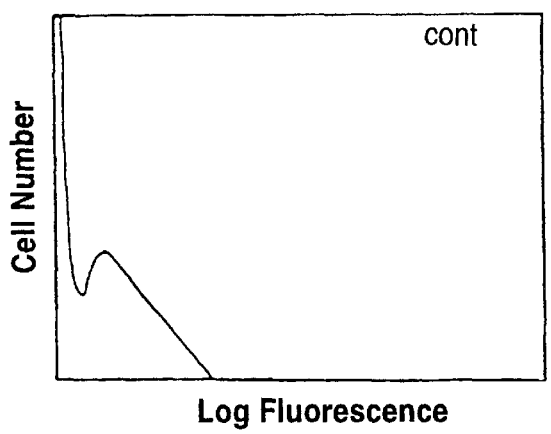
FIG. 1: Expression of CMRF-44 antigen on isolated blood dendritic cells. Dendritic cells were purified from ER⁻PBMC as described below in Materials and Methods by either (a) direct sorting for CD3, CD19, CD57, CD16, CD14 negative cells, or (b) a conventional procedure utilising in vitro culture, density gradients and panning. Blood dendritic cells were labelled with IgM control (cont) or monoclonal antibody CMRF-44 and the immunofluorescent profiles redrawn to scale.
Figure 1C:
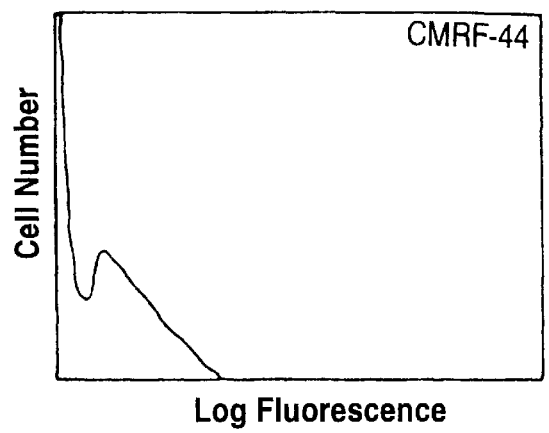
Figure 1B:
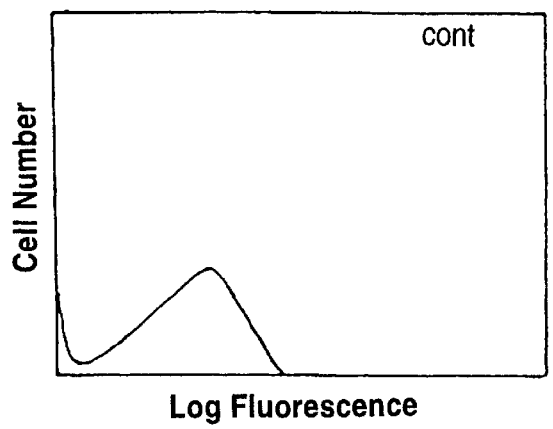
Figure 1D:
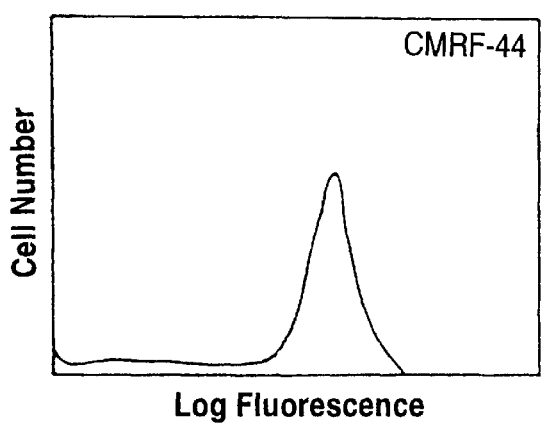
Figure 2A:
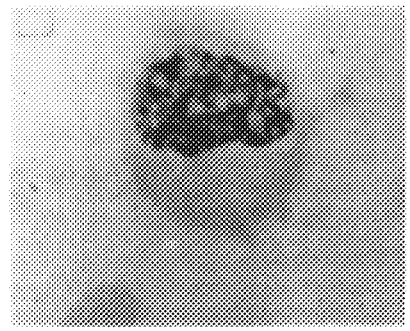
FIG. 2: Tonsil dendritic cells express CMRF-44 antigen. Immunoperoxidase staining of conventionally purified tonsil dendritic cells with (A) IgM control, or (B) monoclonal antibody CMRF-44. Cells were counterstained with haematoxylin and photographed under high power (oil×100)
Figure 2B:
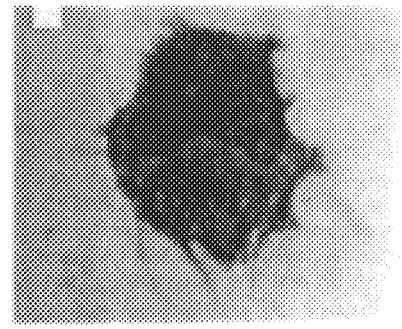

Expression of the CMRF-44 antigen on DC, was examined by both flow cytometry and immunoperoxidase techniques following their isolation by either direct FACS sorting or conventional purification. Isolated DC were characterised by their distinctive morphology, strong allostimulatory activity, intense expression of MHC class II antigens, and lack of reactivity with CD3, CD14, CD16, CD19 and CD57 mAb. Blood DC, when isolated by direct FACS sorting of ER- mononuclear cells (n=3), did not express the CMRF-44 antigen (FIG. 1a). However, when DC were purified by conventional procedures utilising in vitro culture, density gradients and panning, the CMRF-44 antigen was readily detected on these isolated DC populations (FIG. 1b). High density expression of the CMRF-44 antigen was also found on tonsil DC (FIG. 2). It is clear that the CMRF-44 antigen is not expressed on freshly isolated blood DC but is induced during the physical isolation procedures usually used to purify DC. These results readily distinguish CMRF-44 from the BB-1 mAb, which has previously been shown not to react with blood DC prepared by conventional procedures and to only do so after more extensive culture and activation of blood DC (14).

Immunohistological Analysis of CMRF-44 Reactivity

The tissue distribution of the CMRF-44 antigen was examined by immunohistological analysis of different human tissues. Double labelling using anti-HLA-DQ was used to identify Langerhans cells and interstitial DC. No CMRF-44 staining was detected on thymus, spleen, kidney or skin, indicating Langerhans cells and interstital DC do not express the antigen in high density. However, strong staining of germinal centre lymphocytes in secondary B lymphoid follicles was noted. Furthermore staining of scattered interfollicular (T cell zone) cells (perhaps interdigitating cells), was observed in tonsil and a number of reactive lymph node sections, which is consistent with the postulated DC migration/activation pathway (1).

Reactivity of CMRF-44 With Normal Haemopoietic Cells

Peripheral blood and tonsil cell populations were screened for CMRF-44 reactivity by flow cytometry. Granulocytes, platelets, red blood cells, monocytes and E rosette positive (ER⁺) PBMC were unreactive with CMRF-44 (Table 1, see below). A small subpopulation of blood lymphocytes were labelled weakly with CMRF-44 and double labelling with CD20 (n=3) identified these cells as B lymphocytes, comprising approximately 15% of the B cells present (data not shown). Tonsil cells were also examined by flow cytometry and as shown in Table 1, CMRF-44 labelled the majority of ER⁻ tonsil cells whilst the ER⁺ population was again unlabelled.

TABLE 1

Reactivity of CMRF-44 with haemopoietic cell populations

| CELL POPULATION | % of reactive cells |
| --- | --- |
| Erythrocytes (n = 3) | 0 |
| Granulocytes (n = 4) | 0 |
| Platelets (n = 2) | 0 |
| Monocytes (n = 5) | 4 ± 4 |
| PBL (n = 4) | 4 ± 2 |
| Tonsil lymphocytes (n = 6) | 57 ± 5 |
| Tonsil B cells (n = 6) | 71 ± 1 |

Values are mean percentage of positive cells ± SD

Reactivity Against Cell Lines and Transfectants

In order to further characterise CMRF-44 antigen expression a large panel of human cell lines were screened by flow cytometry (Table 2, see below). CMRF-44 reacted strongly with all the Hodgkin's disease derived and B lymphoid cell lines tested but was negative on all T lymphoid or myeloid derived cell lines. This pattern of reactivity on cell lines clearly distinguishes the CMRF-44 antigen from a number of other B lymphocyte associated activation antigens including HB15 (13) which is expressed on T cell lines, from the B-LAST1 (22) and BLAST-2 (23) antigens which are not expressed on the CMRF-44 positive cell line Daudi, and from the AB-1 (24) and B8.7 (25) antigens which are not expressed on B lymphoid lines. The strong staining of CMRF-44 with KM-H2, Raji and Daudi similarly distinguishes it from the anti-IRAC (11) reagent which was also generated by immunisation with LA28. CMRF-44 was further distinguished from anti-HB15 and B7/BB-1 reagents on the basis of its lack of reactivity with B7 and HB15 cDNA transfected Cos cells which were shown to label with the anti BB-1 and HB15 reagents respectively.

TABLE 2

Reactivity of CMRF-44 with haemopoietic cell lines

| T CELL LINES | |
| --- | --- |
| Jurkat | — |
| Molt 4 | (1%) |
| HSB2 | — |
| B CELL LINES | |
| WT49 | ++ |
| MANN | ++ |
| RAJI | +++ |
| DAUDI | ++ |
| JY | +++ |
| MYELOID CELL LINES | |
| U937 | — |
| K562 | — |
| THPI | — |
| Hodgkins CELL LINES | |
| L428 | +++ |
| KMH-2 | ++ |
| HDLM-2 | ++ |

The staining intensities are designated as ranging from +++ strongly positive, to + weakly positive, − not stained. The percentages in parentheses refer to the number of cells stained if less than 95%.

Biochemical Studies

In order to characterise the CMRF-44 antigen a series of immunoprecipitations were carried out with $S^{35}$-methionine and biotin labelled cell lysates of the cell lines L428 and Raji as well as PMA+CaI activated ER⁻ tonsil cells. Preliminary slot blotting experiments with whole cell lysates (data not shown) determined that the CMRF 44 antigen is effectively solubilised by both non-ionic detergents and CHAPS, although CMRF-44 binding to blotted lysate was abrogated by the presence of CHAPS. In view of this apparent sensitivity in the antigen-mAb interaction immunoprecipitations were carried out using both high and low stringency wash protocols. Despite this CMRF-44 failed to precipitate an identifiable protein band although coprecipitation of appropriate molecular weight products with HLA-DR, CD45 and 4F2 reagents, was observed under these conditions.

Subsequent enzyme studies (Table 3, see below) showed that pretreatment of the cell lines Raji and L428 with the enzymes pronase, papain and neuramrinidase either had no effect or increased CMRF-44 binding although the binding of anti-BB-1 and HB15 reagents to L428 was considerably diminished by both pronase and papain (as were the anti-HLA class II reagents tested). HB15 and BB-1 antigen expression was likewise diminished by exposure of the cells to tunicamycin, whereas the level of CMRF-44 binding was increased. This data suggests the CMRF-44 antigen is lipid associated. However, a definite association with cell membrane lipids could not be demonstrated as following partitioning of crude lipid extracts and subsequent slot blotting and immunodetection CMRF-44 reactivity was detectable only in material from the interphase of crude lipid partitions and not the upper (aqueous) and lower (chloroform) phases or the nonlipid fraction. The interphase of crude lipid partitions has been reported to contain both free lipid and proteolipids (26) and we have previously observed the presence of protease sensitive antigens in this phase (unpublished data).

The enzyme digestion and tunicamycin studies provide strong evidence that mAb CMRF-44 recognises a unique new epitope on human DC.

TABLE 3

Enzyme and inhibition studies on CMRF-44 antigen expression

| PRETREATMENT OF | RELATIVE MEAN FLUORESCENT INTENSITY | | |
| --- | --- | --- | --- |
| L428 CELL LINE | CMRF-44 | HB15 | BB-1 |
| Media | 1[a] | 1 | 1 |
| Papain | 1.7 | 0.5 | 0.5 |
| Pronase | 1.6 | 0.4 | 0.4 |
| Neuraminidase | 0.9 | 1 | 1 |
| Tunicamycin | 1.2 | 0.3 | 0.6 |

[a]Defined by control staining of L428 preincubated with media alone

Reactivity of CMRF-44 With Activated Cells

The pattern of CMRF-44 reactivity with different DC populations suggested that mAb CMRF-44 recognises an early activation antigen. We therefore examined CMRF-44 antigen expression following the in vitro activation of isolated cell populations.

CMRF-44 antigen was not expressed on blood or tonsil T lymphocytes during stimulation (three days) with PHA. Stimulation of both blood and tonsil B lymphocytes with low levels of anti-IgM induces a rapid increase in both the percentage of B lymphocytes stained and the intensity of CMRF-44 staining, which was maximal (90% of B cells positive), following 24 hour culture. A similar induction of CMRF-44 antigen expression is observed following culture in media alone. The expression of the B7/BB-1 antigen during anti-IgM stimulation of tonsil B cells was also examined using the BB-1 mAb reagent and was found to be absent until day 3. These results, together with the staining studies on isolated DC provide good evidence that mAb CMRF-44 recognises an activation antigen whose expression is induced prior to the B7/BB-1 antigen.

Figure 3:
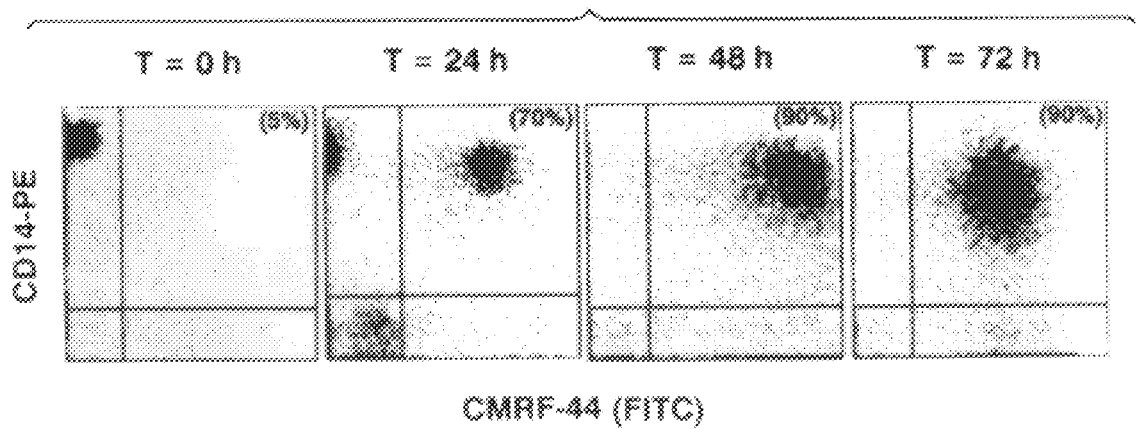
FIG. 3: Expression of CMRF-44 antigen on activated monocytes. ER⁻PBMC were cultured with IFNγ and CMRF-44 antigen induction on monocytes analysed by double labelling with monoclonal antibody CMRF-44 and PE-conjugated anti-CD14. Data are shown as dot plots of CD14 fluorescence intensity against CMRF-44 antigen fluorescence intensity after 0, 24, 48, 72 h of culture. Data are from one representative experiment of three performed.

The expression of the CMRF-44 antigen was inducible only on a small subpopulation of monocytes (10–30%) following 24 h culture in AB medium or AB medium supplemented with GM-CSF or LPS. Culture in the presence of IFN-γ however induced a rapid upregulation of the CMRF-44 antigen (FIG. 3) with maximal antigen expression being detected on 80–90% of monocytes following 48 h culture (n=2).

Figure 4:
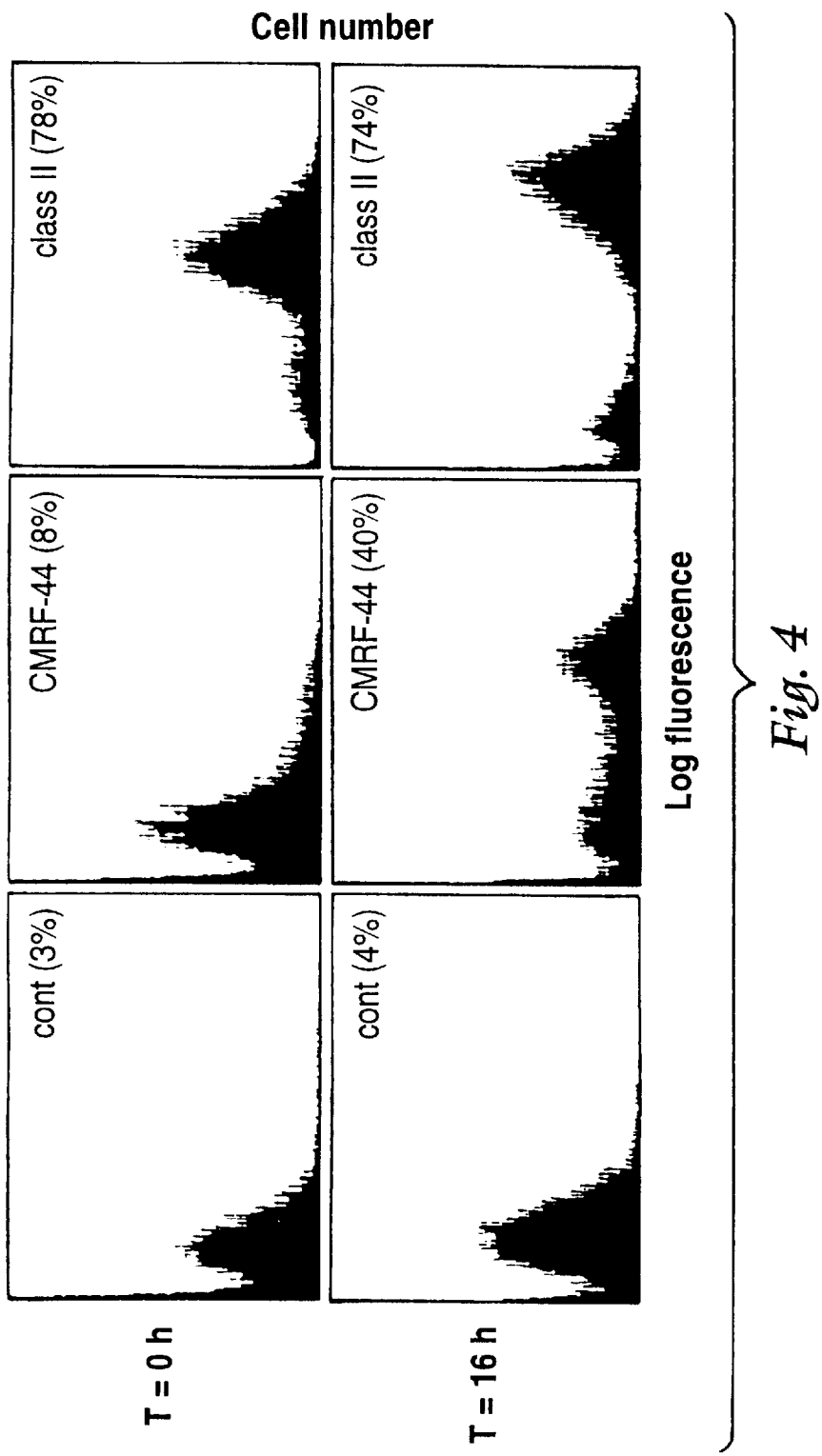
FIG. 4: Expression of CMRF-44 and HLA class II antigens on ER⁻PBMC following in vitro culture (16 h,37° C.). ER⁻PBMC were stained with IgM control (cont), monoclonal antibody CMRF-44 or anti-class II reagent either immediately (T=0 h) or following culture (T=16 h) in media. The data are shown as immunofluorescent profiles and are from a representative experiment of six performed. Figures in brackets indicate the percentage of positive staining detected.

The CMRF-44 antigen is detected on blood DC, only when purified by conventional isolation techniques which involve overnight culture. Double labelling was utilised to examine the induction of CMRF-44 antigen expression on the leucocyte populations of ER⁻ PBMC following overnight culture (16 h, 37° C.) in medium (n=6). Consistent with the previous activation studies, the majority of the B lymphocytes (90%), and a subpopulation of the monocytes (10–30%) present labelled with mAb CMRF-44 following the overnight culture of ER⁻PBMC preparations. Both the T and NK cell populations remain negative. Although the percentage of cultured ER⁻PBMC which label with mAb CMRF-44 varies with the relative size of the monocyte and B lymphocyte populations, CMRF-44 stains 20–40% of most cultured ER-PBMC preparations (FIG. 4). The mAb CMRF-44 positive population in cultured peripheral blood is considerably smaller than that observed following staining of the same preparations with anti-HLA class II reagents, which are commonly used as broad markers of allostimulatory (DC) populations.

CMRF-44 Stains Allostimulatory Populations

Figure 5:
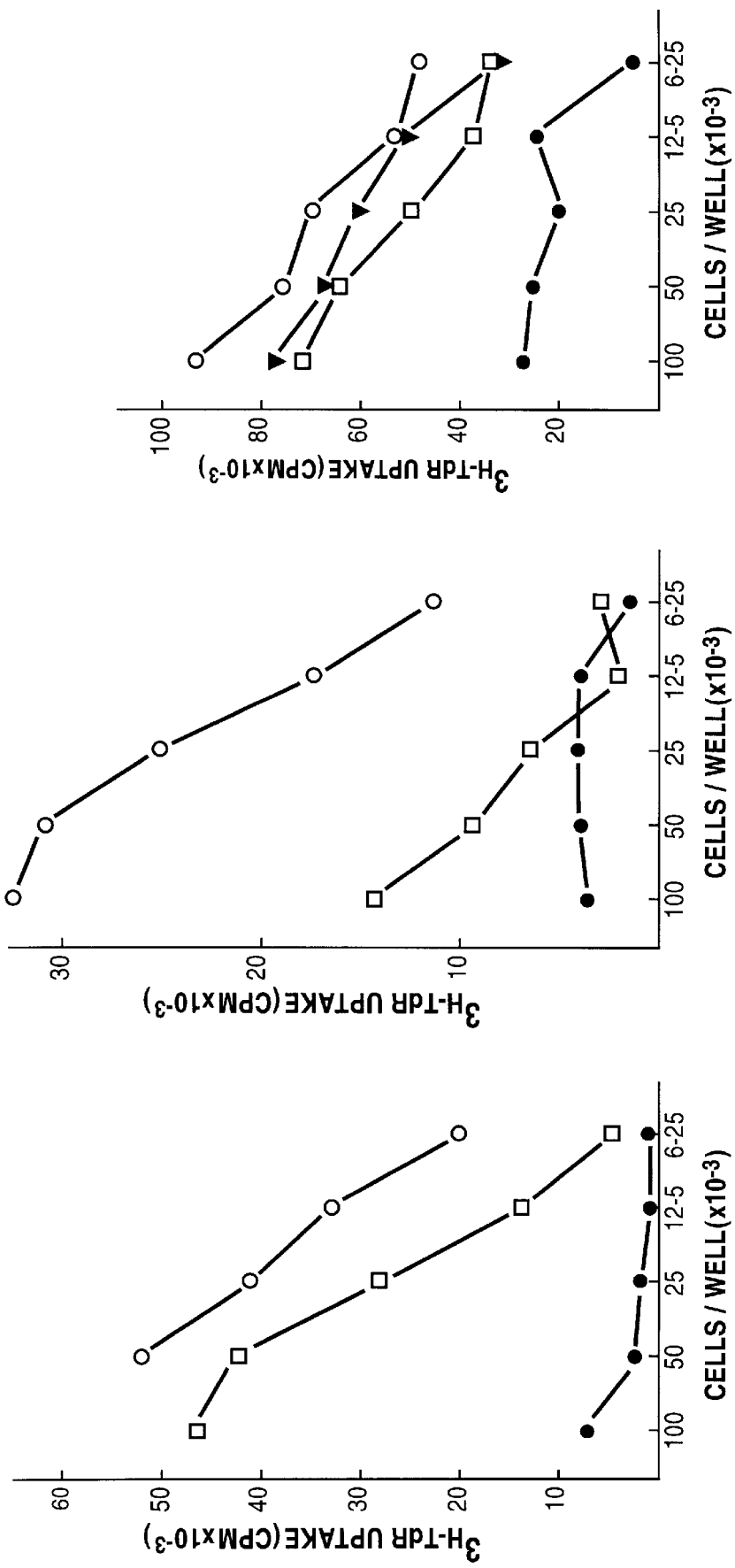
FIG. 5: The CMRF-44 antigen is expressed on the allostimulatory population within cultured blood leukocytes. ER⁻PBMC were cultured overnight in medium and then sorted on the FACS into CMRF-44 positive (○) and negative (●) populations, either before or after further dendritic cell enrichment procedures. Sorted cell populations and monoclonal antibody CMRF-44 labelled (□) and non-labelled (Δ) controls were cultured with allogeneic T lymphocytes for 5 days, then ($^3$H)TdR incorporation determined. Results are expressed as the mean of triplicate counts obtained following sorting of (a) a semipurified dendritic cell preparation obtained from cultured ER⁻PBMC by centrifugation on a BSA gradient and panning as described in Material and Methods; (b) ER⁻PBMC subjected to 16 h in vitro culture alone; (c) the low density (dendritic cell enriched) fraction of cultured ER⁻PBMC obtained by centrifugation on a Nycoprep gradient.

DC are characterised functionally by their potent allostimulatory activity. By comparison other peripheral blood cell populations such as B lymphocytes and monocytes are very inefficient stimulators. Although CMRF-44 was essentially unreactive with freshly isolated PBMC, overnight culture of ER⁻PBMC induces moderate expression of CMRF-44 antigen on a subpopulation of these cultured cells. We therefore examined the ability of the CMRF-44 positive population to stimulate an allogeneic MLR in order to confirm that CMRF-44 reactivity was an effective marker of the activated DC population. Preliminary experiments determined that the presence of CMRF-44 did not affect DC function, ie block an MLR (data not shown). Cultured ER⁻PBMC were sorted on the basis of CMRF-44 reactivity, either before or after further enrichment of allostimulatory (DC) populations. As shown in FIG. 5a, stimulatory cells for the allogeneic MLR were highly enriched in the CMRF-44 positive population (30%) obtained by sorting semipurified DC preparations. In comparison the CMRF-44 negative cells were very weak stimulators. This separation of stimulatory activity was also observed following separation of cultured ER⁻PBMC (FIG. 5b) into CMRF-44 positive (30%) and negative populations. The allostimulatory population within preparations of cultured (16 h, 37° C.) ER⁻PBMC is enriched in the low density fraction obtained by centrifugation on a Nycoprep 1.068 gradient (McLelland, Starling and Hart, unpublished data). Further separation of all the allostimulatory activity within this low density fraction can be achieved by sorting on the basis of CMRF-44 reactivity (FIG. 5c).

These results identify CMF-44 as an early marker of allostimulatory populations within both cultured ER⁻PBMC and semipurified allostimulatory (DC) preparations.

As will be clear from the above, mAb CMRF-44, recognises a novel antigen expressed on subpopulations of human DC. Further, the clear expression of this antigen on conventionally purified blood and tonsil DC, but its absence on Langerhans cells in the skin and unactivated blood DC implied that CMRF-44 recognised an activation antigen. This was confirmed by its cellular reactivity, the CMRF-44 antigen being absent on normal resting leucocytes and cell lines of T and myeloid origin but expressed on B lymphoid lines, a subpopulation of blood B lymphocytes and the majority of tonsil B lymphocytes. Expression of the CMRF-44 antigen was also rapidly induced on blood B lymphocyte (<24 h) and monocyte populations by in vitro activation indicating the CMRF-44 antigen is a very early marker of cellular activation.

The induction of this antigen is remarkable in comparison to other activation antigens, in that it requires only minimal in vitro stimulation, the CMRF-44 reactivity on blood DC and B lymphocytes being readily inducible by overnight culture in media alone. A number of other B lymphocyte associated activation antigens have been described previously and the expression of a number of these antigens has been documented on isolated DC. However, the rapid induction of CMRF-44 antigen expression on B lymphocyte populations clearly distinguishes it from many of these antigens such as BLAST 1 (22), BLAST-2 (CD23) (23), B7/BB-1 (27,28), AB1 (24), B8.7 (25) and B5 (29) whose maximal expression is reported to occur considerably later following activation. The antigens recognised by Ba (CDw78) (30), and Bac-1 (31),occur earlier after B lymphocyte activation but their expression on other activated leucocyte populations is unknown.

The novel activation antigen CMRF-44 recognised by mAb CMRF-44 forms part of the present invention, together with its biological equivalents expressed by DC of animals other than humans.

Industrial Application

There are a number of uses to which the antibodies of the invention (which recognise and bind to the activation antigen CMRF-44 and its equivalents) can be put. Such uses include (1) the identification (for diagnostic purposes) of activated DC; and (2) the purification/concentration of activated DC, and these uses accordingly represent further aspects of this invention.

Diagnostic applications of the present exemplary mAb CMRF-44 include allowing for assessment of activated (CMRF-44 positive) against non-activated (CMRF-44 negative) DC, which may be of use in the diagnosis and/or therapy of diseases such as leukaemia or lymphoma.

In such applications, any immunological-based assay procedures known in the art could be employed for quantifying the amount of activated DC in a sample. Such procedures are summarised in Tijssen (39) such as flow cytometry, ELISA, RIA and fluorescence microscopy among others.

In terms of isolation of activated DC, once again any process or purification system which employs the antibodies (or their binding fragments) as the primary immunological reagent can be used. Many such processes are known, as are purification systems which allow for these processes to be put into effect. An example of a commercially available purification system is the avidin-biotin immunoaffinity system (44) from CellPro, Inc., Washington, USA See also U.S.

Pat. Nos. 5,215,927, 5,225,353, 5,262,334, 5,240,856 and PCT/US91/07646 published 30 Apr. 1992, all incorporated herein by reference. This system employs directly or indirectly a biotinylated monoclonal antibody directed against a target cell and a column containing immunobilized avidin and can be readily adapted to extract activated human dendritic cells, in this case from human peripheral blood, using the exemplary mAb CMRF-44 as follows:

1. A sample of human peripheral blood containing the human dendritic cells is mixed with biotinylated mAb CMRF-44 and incubated to allow formation of mAb CMRF-44/human DC complexes.
2. Following incubation, the mixture is introduced into a CellPro continuous-flow immunoadsorption column filled with avidin-coated beads, the strong affinity between biotin and avidin causing the biotin-coated mAb CMRF-44 (together with the human DC to which they have bound) to adhere to the avidin-coated beads.
3. After unwanted cells present in the mixture are washed away, captured activated human DC are removed from the column by gentle agitation and are available for use.

Variations on this theme using mAb CMRF-44 as primary antibody (to bind to activated DC) and a biotinylated secondary antibody (to bind to mAb CMRF-44) can also be employed.

It will be appreciated that before admixture with mAb CMRF-44 in accordance with the above protocol, the human peripheral blood sample should be treated to ensure that the DC the sample contains are activated. This can easily be achieved by, for example, overnight incubation of the sample.

For use in the above protocol, mAb CMRF-44 can be biotinylated by any one of a number of conventional methods. For example, the biotinylation procedure of Berenson et al (44) can be employed.

A possible and preferred preliminary step in the methods outlined above is the enrichment of DC in the sample by gradient centrifugation (40–42). While this optional enrichment step can employ any suitable known gradient medium (such as albumin or metrizamide), it is however preferred that a Nycodenz medium (Nycomed Pharma, Oslo, Norway) be used (43) in relation to 16 hour cultured T lymphocyte-depleted peripheral blood mononuclear cells. The applicants have found that use of this gradient reliably yields a population of low density cells that is highly enriched for DC.

It will be apparent to one skilled in the art that there are numerous other means of immunoselection of dendritic cells, in addition to avidin-biotin immunoaffinity chromatography. These include, but are not limited to, immunoselection using magnetic beads, ferrofluids, dipsticks, petri dishes, and a wide variety of other solid phases that can be derivatized so as to specifically bind CMRF-44 labelled DC.

Once purified/concentrated by the above or any other suitable process, the activated DC can be employed in research or in commercial applications. One such potentially commercial application for activated DC is as part of an immunopotentiating composition together with an antigen protective against disease, for either prophylaxis or therapy. It is believed that such compositions would increase both the speed and efficiency of the immune response generated against the protective antigen.

Other applications of the activated DC (or of the activation antigen CMRF-44) will of course be apparent to those persons skilled in this art.

It will be understood that the above description is exemplary only and that the present invention is not limited thereto.

REFERENCES

1. Steinman, R. M. 1991.The dendritic cell system and its role in immunogenicity. Ann Rev. Immunol. 9:271.
2. Macpherson, G. G. 1989. Lymphoid dendritic cells: their life history and roles in immune responses. Res. Immunol. 140:877.
3. Hart, D. N. J. and J. L. McKenzie. 1990. Interstitial dendritic cells. Intern Rev Immunol. 6:127.
4. Steinman, R. M., B. Gutchinov, M. D. Witmer, and M. C. Nussenweig. 1983. Dendritic cells are the primary stimulators of the primary mixed lymphocyte reaction in mice. J. Exp. Med. 147:613.
5. Inaba, K., M. D. Witmer-Pack, and R. M. Steinman. 1984. Clustering of dendritic cells, helper T lymphocytes and histocompatibaility B cells during primary T cell responses in vitro. J. Exp. Med. 160:858.
6. Kuntz Crow, M. and H. G. Kunkel. 1982. Human dendritic cells: major stimulators of the autologous and allogeneic mixed leucocyte reactions. Clin. Exp. Immunol. 49:338.
7. Thomas, R., L. S. Davis, and P. E. Lipsky. 1993. Isolation and characterization of human peripheral blood dendritic cells. J Immunol 150:821.
8. Hart, D. N. J., and J. L. McKenzie. 1988. Isolation and characterization of human tonsil dendritic cells. J Exp Med 168:157.
9. Prickett, T. C. R., J. L. McKenzie, and D. N. J. Hart. 1992. Adhesion molecules on human tonsil dendritic cells. Transplantation 53:483.
10. Freudenthal, P. S., and R. M. Steinman. 1990. The distinct surface of human blood dendritic cells, as observed after an improved isolation method. PNAS 87:7698.
11. Hart, D. N. J., and T. C. R. Prickett. 1993. Intercellular adhesion molecule-2 (ICAM-2) expression on human dendritic cells. Cellular Immunol. 148:447.
12. Hsu, P. L. and S. M. Hsu. 1990. Identification of an Mr 70,000 antigen associated with Reed-Sternberg cells and interdigitating reticulum cells. Cancer Res. 50:350.
13. Zhou, L. J, R Schwarting, H. M. Smith, and T. F. Tedder. 1992. A novel cell surface molecule expressed by human interdigitating reticulum cells, Langerhans cells, and activated lymphocytes is a new member of the Ig superfamily. J Immunol. 149:735.
14. Hart, D. N. J., G. C. Starling, V. L. Calder, and N. S. Fernando. 1993. B7/BB-1 is a leucocyte differentiation antigen on human dendritic cells induced by activation. Immunol 79:616.
15. McKenzie, J. L., W. Egner, V. L. Calder, and D. N. J. Hart. 1992. Hodgkin's disease cell lines: a model for interleukin-1-independent accessory cell function. Immunol 77:345.
16. Kadin, M. E. 1982. Possible origin of the Reed-Sternberg cell from an interdigitating reticulum cell. Cancer Treat. Rep. 66:601.
17. Hsu, S. M. 1990. The never ending controversies in Hodgkin's disease. Blood 75:1742.
18. Cole, S. R., L. K. Ashman, and P. L. Ey. 1987. Biotinylation: an alternative to radioiodination for the identification of cell surface antigens in immunoprecipitates. Mol. Immunol. 24:699.
19. Tedder, T. F., G. McIntyre, and S. F. Schlossman. 1988. Heterogeneity in the B1 (CD20) cell surface molecule expressed by human B-lymphocytes. *Mol. Immunol.* 25:1321

20. Magnani, J. L., M. Brockhaus, D. F. Smith, and V. Ginsburg. 1981. A monosialoganglioside is a monoclonal antibody-defined antigen of colon carcinoma. *Science* 212:55.

21. Bligh, E. G., and W. J. Dwyer. 1959. A rapid method of total lipid extraction and purification. *Can. J. Biochem. Physiol.* 37:911.

22. Thorley-Lawson, D. A., R. T. Schooley, A. K. Bhan, and L. M. Nadler. 1982. Epstein-Barr virus superinduces a new human B cell differentiation antigen (B-Last 1) expressed on transformed lymphoblasts. *Cell* 30:415.

23. Thorley-Lawson, D. A., L. M. Nadler, A. K. Bhan, and R. T. Schooley. 1985. BLAST-2 (EBVCS), an early cell surface marker of human B cell activation, is superinduced by Epstein Barr virus. *J. Immunol.* 134:3007.

24. Jung, L. K. L., and S. M. Fu. 1984. Selective inhibition of growth factor dependent human B cell proliferation by monoclonal antibody ABI to an antigen expressed by activated B cells. *J. Exp. Med.* 160:1919.

25. Leprince, C., Y. Richard, P. Krief, D. Treton, C. Boucheix, and P. Galanaud. 1988. A B cell restricted activation antigen (B8.7) functionally related to the low molecular weight B cell growth factor receptor. *J. Immunol.* 140:100.

26. Folch, J., and M. Lees. 1951. Proteolipids, a new type of tissue lipoproteins. *J. Biol. Chem.* 191:807.

27. Yokochi, T., R. D. Holly, and E. A. Clark. 1982. B lymphoblast antigen (BB-1) expressed on Epstein-Barr virus-activated B cell blasts, B lymphoblastoid cell lines and Burkitt's lymphomas. *J. Immunol.* 128:823.

28. Freedman, A. S., G. Freeman, J. C. Horowitz, J. Daley, and L. M. Nadler. 1987. B7, a B-cell restricted antigen that identifies preactivated B cells. *J. Immunol.* 139:3260.

29. Freedman, A. S., A. W. Boyd, K. C. Anderson, D. C. Fisher, S. F. Schlossman, and L. M. Nadler. 1985. B5, a new B cell-restricted activation antigen. *J. Immunol.* 134:2228.

30. Kikutani, H., R. Kimura, H. Nakamura, R. Sato, A. Muraguchi, N. Kawamura, R. R. Hardy, and T. Kishimoto. 1986. Expression and function of an early activation marker restricted to human B cells. *J. Immunol.* 136:4016.

31. Suzuki, T., S. K. Sanders, J. L. Butler, G. L. Gartland, K. Komiyama, and M. D. Cooper. 1986. Identification of an early activation antigen (Bac-1) on human B cells. *J. Immunol.* 137:1208.

32. Freudentol and R. M. Steinman. 1990. The distinct surface of human blood dendritic cells, as observed after an improved isolation method. *Proc. Natl. Acad. Sci. USA* 89:1698.

33. J. P. Meilay, H. D. Witmer-Park, R. Agger, M. T. Crowley, D. Lawless and R. M. Steinman. (1990) The distinct leukocytic antigens of mouse spleen dendritic cells as identified with new hamster monoclonal antibodies. *J. Exp. Med.* 171:1753.

34. U. O'Doherty, W. J. Swiggand, K. Inaba, Y. Yamaguchi, I. Kopelaff, N. Bhardwaj and R. M. Steinman. (1993) Tolerizing Mice to human leukocytes; A step towards the production of monoclonal antibodies specific for human dendritic cells. *Dendritic Cells in Fundamental and Clinical Immunology*, Plenum Press, New York, 165–172.

35. Kohler G. and Milstein C. (1975) Continuous Cultures of Fused Cells Secreting Antibody of Predefined Specificity. *Nature* 256:495–497.

36. Tjissen P. (1990) Practice and Theory of Enzyme Immunoassays. *Laboratory Techniques in Biochemistry and Molecular Biology,* Elsevier, Amsterdam, New York, Oxford 117–121.

37. Hodgson J. (1991) Making Monoclonals in Microbes. *Biotechnology* 9:423–425.

38. Sundstrom C., Nilsson K. (1976) Establishment and characterisation of a human histiocytic lymphoma cell line (U937). *Int. J Cancer* 17:565.

39. V. Diehl, H. H. Kirchner, H. Burrichter, H. Stein, C. Fonatsch, J. Gerdes, M. Schaadt, W. Heit, B. Uchanska-Ziegler, A. Ziegler, F. Heintz and K. Sueno. (1982) Characteristics of Hodgkins Disease-Derived Cell Lines. *Cancer Treat Rep.* 66:615–632.

40. Van Voorhis, W. C., Hair L., Steinman K., Kaplan G. (1982) Human Dendritic Cells. *J. Exp. Med.* 155:1172.

41. Knight S. C., Farrant J. Bryant A., Edwards A. J., Burman S., Lever A., Clark J., Webster A. D. B. (1986) Non-adherent low density cells from human peripheral blood contain dendritic cells and monocytes both with vieled morphology. *Immunology* 57:595.

42. Young J. W., Steinman R. M. (1988) Accessory cell requirements for the mixed leukocyte reaction and polyclonal mitogens as studied with a new technique for enriching blood dendritic cells. *Cellular Immunology* 111:167.

43. Boyum A. (1983). Isolation of human blood monocytes with Nycodenz, a new non-ionic iodinated gradient medium. *Scand J. Immunology* 17, 429–436.

44. Berenson R. J., Bensinger W. I., Kalamasz D. (1986) Positive selection of Viable Cell Populations Using Avidin-Biotin Immunoadsorption. *Journal of Immunological Methods* 91:11.

45. Harlow and Lane (1988) Antibodies: A Laboratory Manual. *Cold Spring Harbor Press* 144.

I claim:

1. Hybridoma cell line CMRF-44(ATCC CRL 11482).

2. Monoclonal antibody CMRF-44 which is secreted by hybridoma cell line CMRF-44 (ATCC CRL 11482) which binds to an epitope on activated human dendritic cells.

3. A process for purifying activated dendritic cells from a sample containing such activated dendritic cells comprising the steps of:

(i) contacting said sample with monoclonal antibody CMRF-44 produced by hybridoma ATCC CRL 11482; and (ii) recovering activated dendritic cells which have bound to said antibody.

4. A purification system for use in purifying and/or concentrating activated dendritic cells from a sample containing such cells which includes monoclonal antibody CMRF-44 produced by hybridoma ATCC CRL 11482.

5. A purification system as claimed in claim 4 in which antibody CMRF-44 is biotinylated.

* * * * *